(12) United States Patent
Flury et al.

(10) Patent No.: US 11,839,399 B2
(45) Date of Patent: *Dec. 12, 2023

(54) ROTATIONAL MEDICAL DEVICE

(71) Applicant: BOSTON SCIENTIFIC LIMITED, Hamilton (BM)

(72) Inventors: Kristi Mae Flury, Maple Grove, MN (US); Sharath Badadamath, Hosapete (IN)

(73) Assignee: BOSTON SCIENTIFIC LIMITED, Hamilton (BM)

(*) Notice: Subject to any disclaimer, the term of this patent is extended or adjusted under 35 U.S.C. 154(b) by 0 days.

This patent is subject to a terminal disclaimer.

(21) Appl. No.: 17/724,172

(22) Filed: Apr. 19, 2022

(65) Prior Publication Data
US 2022/0240975 A1 Aug. 4, 2022

Related U.S. Application Data

(63) Continuation of application No. 16/380,587, filed on Apr. 10, 2019, now Pat. No. 11,331,119.
(Continued)

(51) Int. Cl.
*A61B 17/00* (2006.01)
*A61B 17/3207* (2006.01)
(Continued)

(52) U.S. Cl.
CPC .. *A61B 17/320758* (2013.01); *A61B 17/3207* (2013.01); *A61B 2017/00017* (2013.01);
(Continued)

(58) Field of Classification Search
CPC ........ A61B 17/3207; A61B 17/320708; A61B 17/320725; A61B 17/320733;
(Continued)

(56) References Cited

U.S. PATENT DOCUMENTS 5,779,722 A 7/1998 Shturman et al.
6,024,749 A 2/2000 Shturman et al.
(Continued)

FOREIGN PATENT DOCUMENTS

EP 0268228 A2 5/1988
JP 2013520280 A 6/2013

OTHER PUBLICATIONS http://www.mikipulley.co.jp/EN/Products/Electoromagnetic-ClutchesAndBrakes/ElectoromagneticActuatedTypeClutchAndBrakeUnits/index.html. 4 Pages. Downloaded Jul. 10, 2019.
(Continued)

*Primary Examiner* — Majid Jamialahmadi
(74) *Attorney, Agent, or Firm* — Seager, Tufte & Wickhem, LLP

(57) ABSTRACT

Medical systems and methods for making and using medical systems are disclosed. Example medical systems may include an atherectomy system configured to engage and remove plaque from walls in vessels of a vascular system. The atherectomy system may include a drive shaft, a rotational tip coupled to an end of the drive shaft, a drive mechanism coupled to the drive shaft to rotate the rotational tip, and control configurations to control settings of operational modules of the atherectomy system. The control configurations may be configured to change settings of multiple operational modules of the atherectomy system in response to a single actuation of an actuator to facilitate use of the atherectomy system in a vasculature of a patient.

13 Claims, 11 Drawing Sheets

Related U.S. Application Data

(60) Provisional application No. 62/655,593, filed on Apr. 10, 2018.

(51) Int. Cl.
- *A61B 17/32* (2006.01)
- *A61B 17/22* (2006.01)
- *A61B 90/00* (2016.01)

(52) U.S. Cl.
CPC ............... *A61B 2017/00115* (2013.01); *A61B 2017/00128* (2013.01); *A61B 2017/00132* (2013.01); *A61B 2017/00526* (2013.01); *A61B 2017/22049* (2013.01); *A61B 2017/320004* (2013.01); *A61B 2017/320766* (2013.01); *A61B 2090/031* (2016.02)

(58) Field of Classification Search
CPC  A61B 17/320758; A61B 2017/320766; A61B 2017/320775; A61B 2017/320004
See application file for complete search history.

(56) References Cited

U.S. PATENT DOCUMENTS

| | | |
|---|---|---|
| 9,844,390 B2 | 12/2017 | Rydberg |
| 2002/0007190 A1 | 1/2002 | Wulfman et al. |
| 2010/0125253 A1 | 5/2010 | Olson et al. |
| 2010/0274270 A1 | 10/2010 | Patel et al. |
| 2011/0213391 A1* | 9/2011 | Rivers ............ A61B 17/320758 606/159 |
| 2015/0164542 A1 | 6/2015 | Wulfman et al. |
| 2016/0374716 A1 | 12/2016 | Kessler et al. |

OTHER PUBLICATIONS https://www.amazon.com/Swingline-Trimmer-Capacity-SmartCut-EasyBlade/dp/B001CE3AUU. 10 Pages. Downloaded Jul. 11, 2019.
International Search Report and Written Opinion dated Jul. 5, 2019 for International Application No. PCT/US2019/026801.

* cited by examiner

ROTATIONAL MEDICAL DEVICE

CROSS-REFERENCE TO RELATED APPLICATIONS

This application is a continuation of U.S. application Ser. No. 16/380,587, filed Apr. 10, 2019, which claims the benefit of priority under 35 U.S.C. § 119 of U.S. Provisional Application No. 62/655,593, filed Apr. 10, 2018, the entire disclosure of which is hereby incorporated by reference.

TECHNICAL FIELD

The present disclosure pertains to medical devices, and methods for manufacturing and using medical devices. More particularly, the present disclosure pertains to rotational medical devices, methods, and systems, including those with multi-functional control elements.

BACKGROUND

A wide variety of medical devices have been developed for medical use, for example, for use in accessing body cavities and interacting with fluids and structures in body cavities. Some of these devices may include guidewires, catheters, pumps, motors, controllers, filters, grinders, needles, valves, and delivery devices and/or systems used for delivering such devices. These devices are manufactured by any one of a variety of different manufacturing methods and may be used according to any one of a variety of methods. Of the known medical devices and methods, each has certain advantages and disadvantages.

BRIEF SUMMARY

This disclosure provides, design, material, manufacturing method and use alternatives for medical devices and systems. In a first aspect, an advancer assembly for an atherectomy device may include a housing, a drive mechanism positioned within the housing, an actuation mechanism in communication with the drive mechanism and accessible from exterior of the housing, and the actuation mechanism adjusts a setting of a first operation module of the advancer assembly and a setting of a second operation module of the advancer assembly upon adjustment of the actuation mechanism.

In addition or alternative and in a second aspect, the first operation module of the advancer assembly for the atherectomy device may be a speed module configured to adjust a speed setting of the drive mechanism between a first speed setting, a second speed setting, and a zero speed setting in response to the adjustment of the actuation mechanism.

In addition or alternative and in a third aspect, an actuation of the actuation mechanism of the advancer assembly for the atherectomy device may further initiate actuation of the drive mechanism according to the adjusted speed setting.

In addition or alternative and in a fourth aspect, the advancer assembly for an atherectomy device may include a third operation module of the advancer assembly, which may be a lock module configured to activate or deactivate a lock assembly, wherein the adjustment of the actuation mechanism deactivates the lock assembly.

In addition or alternative and in a fifth aspect, the second operation module of the advancer assembly may be a braking module configured to activate or deactivate a braking assembly configured to engage a guidewire extending through the housing in response to the adjustment of the actuation mechanism.

In addition or alternative and in a sixth aspect, the actuation of the actuation mechanism of the advancer assembly for an atherectomy device may adjust a setting of a third operation module of the advancer assembly.

In addition or alternative and in a seventh aspect, the third operation module of the advancer assembly may be a lock module configured to activate or deactivate a lock assembly in response to the adjustment of the actuation mechanism.

In addition or alternative and in an eighth aspect, the actuation mechanism of the atherectomy device may comprise a knob that is axially slidable along the housing.

In addition or alternative and in a ninth aspect, the adjustment of the actuation mechanism may be a first adjustment of the actuation mechanism, and a second adjustment of the actuation mechanism may further adjust the setting of the first operation module of the advancer assembly and the setting of the second operation module of the advancer assembly.

In addition or in alternative and in a tenth aspect, an atherectomy device may comprise an advancer assembly having a knob assembly, a rotation assembly in communication with the advancer assembly, wherein the knob assembly may be longitudinally adjustable to advance and retract the rotation assembly, and wherein adjustment of the knob assembly may be configured to adjust a lock setting for the knob assembly and a speed setting on which a rotation of the rotation assembly is based.

In addition or in alternative and in an eleventh aspect, the adjustment of the knob assembly of the atherectomy device may be further configured to adjust a setting for a brake assembly of the advancer assembly.

In addition or in alternative and in a twelfth aspect, the advancer assembly of the atherectomy device may comprise a housing and a drive mechanism positioned within the housing.

In addition or in alternative and in a thirteenth aspect, the knob assembly of the atherectomy device may be in communication with the drive mechanism and may be accessible from an exterior of the housing.

In addition or in alternative and in a fourteenth aspect, the rotation assembly of the atherectomy device may comprise an elongate member coupled to a rotational device at a distal end of the elongate member.

In addition or in alternative and in a fifteenth aspect, the knob assembly of the atherectomy device may be in communication with the drive mechanism and the drive mechanism may be configured to rotate the elongate member based on the speed setting.

In addition or in alternative and in a sixteenth aspect, the knob assembly of the atherectomy device may be in electrical communication with the drive mechanism.

In addition or in alternative and in a seventeenth aspect, a method of operating an atherectomy device may comprise adjusting an actuator of an advancer assembly of the atherectomy device a first time to adjust a speed setting of a drive mechanism to a first speed setting of a plurality of speed settings and adjust a brake setting of a brake module between a deactivated state setting and an activated state setting, longitudinally translating the actuator to advance the advancer assembly, and adjusting the actuator of the advancer assembly a second time after longitudinally translating the actuator.

In addition or alternative and in an eighteenth aspect, actuating the actuator may activate or deactivate a lock assembly of the advancer assembly.

In addition or alternative and in a nineteenth aspect, the actuation of the actuator the first time may adjust the setting of the speed of the drive mechanism to an advance speed and may adjust the brake setting to the activated state setting.

In addition or alternative and in a twentieth aspect, the adjusting of the actuator the second time may adjust the setting of the speed of the drive mechanism to a zero speed and may adjust the brake setting to the deactivated state setting.

BRIEF DESCRIPTION OF THE DRAWINGS

The invention may be more completely understood in consideration of the following detailed description of various embodiments of the invention in connection with the accompanying drawings, in which.

Figure 1:
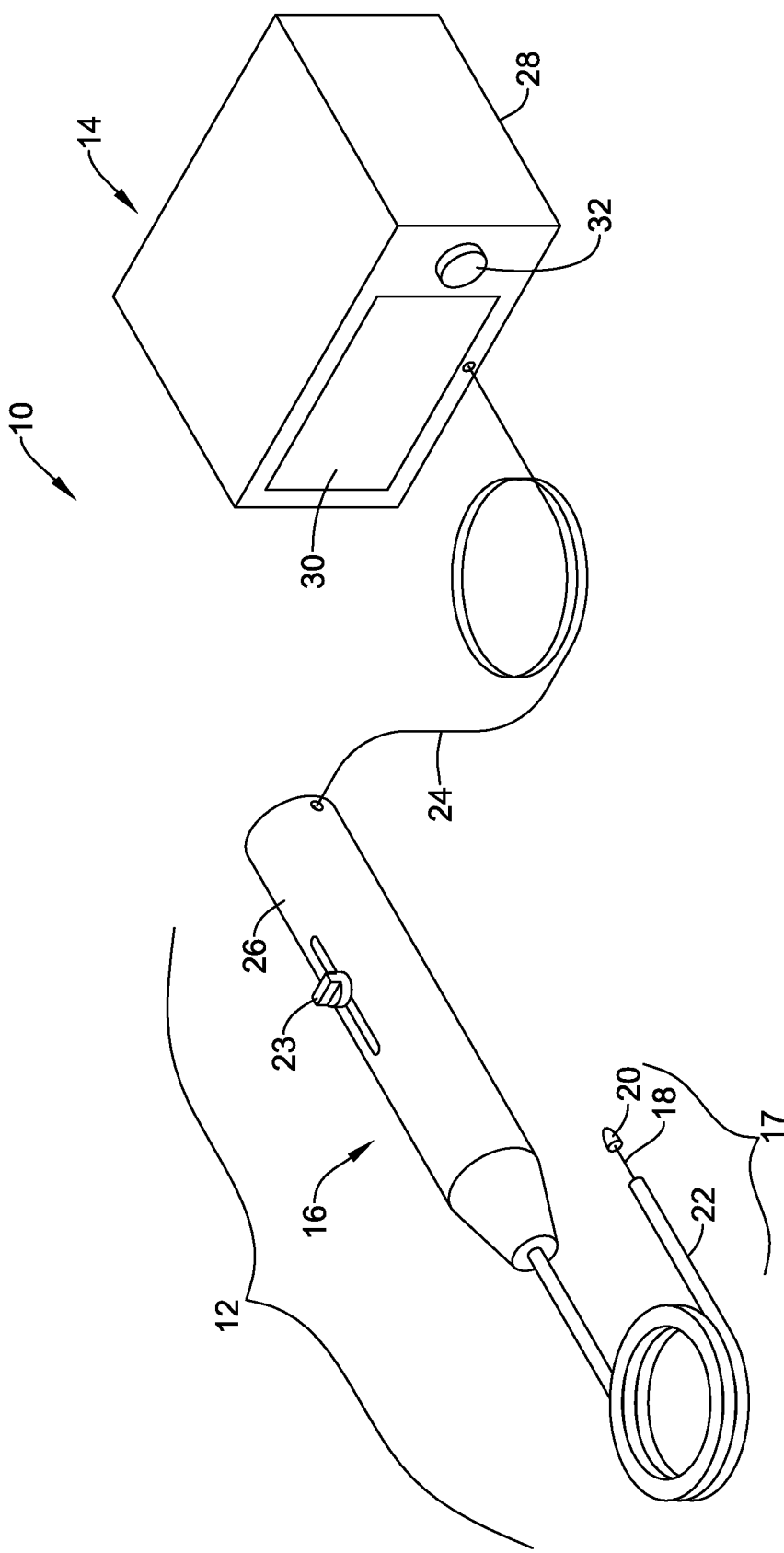
FIG. 1 is a schematic diagram of an example atherectomy system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Cardiovascular disease and peripheral arterial disease may arise from accumulation of atheromatous material on the inner walls of vascular lumens, resulting in a condition known as atherosclerosis. Atheromatous and other vascular deposits may restrict blood flow and can cause ischemia in a heart of a patient, vasculature of a patient's legs, a patient's carotid artery, etc. Such ischemia may lead to pain, swelling, wounds that will not heal, amputation, stroke, myocardial infarction, and/or other conditions.

Atheromatous deposits may have widely varying properties, with some deposits being relatively soft and others being fibrous and/or calcified. In the latter case, the is deposits may be referred to as plaque. Atherosclerosis occurs naturally as a result of aging, but may also be aggravated by factors such as diet, hypertension, heredity, vascular injury, and the like. Atherosclerosis may be treated in a variety of ways, including drugs, bypass surgery, and/or a variety of catheter-based approaches that may rely on intravascular widening or removal of the atheromatous or other material occluding the blood vessel. Atherectomy is a catheter-based intervention that may be used to treat atherosclerosis.

Atherectomy in an interventional medical procedure performed to restore a flow of blood through a portion of a patient's vasculature that has been blocked by plaque or other material (e.g., blocked by an occlusion). In an atherectomy procedure, a device on an end of a drive shaft that is used to engage and/or remove (e.g., abrade, grind, cut, shave, etc.) plaque or other material from a patient's vessel (e.g., artery or vein). In some cases, the device on an end of the drive shaft may be abrasive and/or may otherwise be configured to remove plaque from a vessel wall or other obstruction in a vessel when the device is rotating and engages the plaque or other obstruction.

FIG. 1 depicts an atherectomy system 10. The atherectomy system 10 may be electrically driven, pneumatically driven and/or driven in one or more other suitable manners. Additional or alternative components to those illustrated and described herein may be utilized in the operation of the atherectomy system 10.

The atherectomy system 10 may include a drive assembly 12 and a control unit 14 (e.g., a controller). The drive assembly 12 may include, among other elements, an advancer assembly 16 and a rotation assembly 17. Although the control unit 14 is depicted as being separate from the drive assembly 12 in FIG. 1, the functionality of the control unit 14 and the drive assembly 12 may be incorporated into a single component (e.g., in the advancer assembly 16 or other suitable single component).

The rotation assembly 17 may include a drive shaft 18 (e.g., an elongate member that may be or may include a flexible drive shaft or other suitable drive shaft), a rotational device 20 (e.g., a rotational tip or other rotational device), and an elongate member 22 having a first end (e.g., a proximal end), a second end (e.g., a distal end), and a lumen extending from the first end to the second end for receiving the drive shaft 18. In some cases, the elongate member 22 may be an elongated tubular member. The rotational device 20 may have a rough or sharp surface, such that it is configured to grind, abrade, cut, shave, etc. plaque from a vessel wall or other obstruction in a vessel when it is rotated.

The advancer assembly 16 may include a knob 23, a housing 26, a drive mechanism (e.g., the drive mechanism 34 shown, for example, in FIG. 2), and/or one or more other suitable components. The housing 26 may at least partially house the drive mechanism and the knob 23 may be at least partially accessible from an exterior of the housing 26. The drive mechanism may be or may include a motor (e.g., an electric motor, pneumatic motor, or other suitable motor) at least partially housed within the housing 26 and in communication with the knob 23, the drive shaft 18, and the control unit 14. The knob 23 may be configured to advance along a longitudinal path to longitudinally advance the drive mechanism 34 and the rotation assembly 17.

The drive mechanism may be coupled to the drive shaft 18 in a suitable manner including, but not limited to, a weld connection, a clamping connection, an adhesive connection, a threaded connection, and/or other suitable connection configured to withstand rotational speeds and forces. As the drive shaft 18 may rotate over a wide range of speeds (e.g., at speeds of between zero (0) RPM and 250,000 RPM or higher), the coupling between the drive mechanism and the drive shaft 18 may be configured to withstand such rotational speeds and associated forces.

The drive shaft 18 may be formed from one or more of a variety of materials. For example, the drive shaft 18 may be formed from one or more of a variety of materials, including steel, stainless steel, other metal, polymer, and/or other suitable materials.

The drive shaft 18 may have a suitable diameter and/or length for traversing vasculature of a patient. The diameter and/or the length of the drive shaft 18 may depend on the dimension of the lumen of the elongate member 22, the dimensions of vessels of a patient to be traversed, and/or one or more other suitable factors. In some cases, the drive shaft 18 may have a diameter in a range from about 0.030 centimeters (cm) or smaller to about 0.150 cm or larger and a working length in a range from about ten (10) cm or shorter to about three hundred (300) cm or longer. In one example, the drive shaft 18 may have a diameter of about 0.05715 cm and a length of about fifty (50) cm. Alternatively, the drive shaft 18 may have a different suitable diameter and/or different suitable length.

The rotational device 20 may have an outer perimeter which is equal to or larger than a distal diameter of the drive shaft 18 and/or the elongate member 22. Alternatively or in addition, the rotational device 20 may have an outer perimeter which is smaller than a diameter of the drive shaft 18 and/or the elongate member 22. The rotational device 20 may have a symmetric design so that it penetrates equally well in both rotational directions, but this is not required and the rotational device 20 may be configured to penetrate in only one direction.

The rotational device 20 may be coupled to the drive shaft 18. Where the drive shaft 18 has a first end portion (e.g., a proximal end portion) and a second end portion (e.g., a distal end portion), the rotational device 20 may be coupled to the drive shaft 18 at or near the second end portion. In some cases, the rotational device 20 may be located at or adjacent a terminal end of the second end portion of the drive shaft 18.

The rotational device 20 may be coupled to the drive shaft 18 in any manner. For example, the rotational device 20 may be coupled to the drive shaft 18 with an adhesive connection, a threaded connection, a weld connection, a clamping connection, and/or other suitable connection configured to withstand rotational speeds and forces. Similar to as discussed above with respect to the connection between the drive shaft 18 and the drive mechanism, as the drive shaft 18 and/or the rotational device 20 may rotate at speeds between zero (0) RPM and 250,000 RPM or higher, the coupling between the drive shaft 18 and the rotational device 20 may be configured to withstand such rotational speeds and associated forces.

The drive assembly 12 and the control unit 14 may be in communication and may be located in or may have a same housing and/or located in or have separate housings (e.g., the advancer assembly housing 26 and a control unit housing 28 or other housings). Whether in the same housing or in separate housings, the drive assembly 12 and the control unit 14 may be in communication through a wired connection (e.g., via one or more wires in an electrical connector 24 or other suitable electrical connector) and/or a wireless connection. Wireless connections may be made via one or more communication protocols including, but not limited to, cellular communication, ZigBee, Bluetooth, Wi-Fi, Infrared Data Association (IrDA), dedicated short range communication (DSRC), EnOcean, and/or any other suitable common or proprietary wireless protocol, as desired.

Although not necessarily shown in FIG. 1, the drive assembly 12 may include and/or enclose one or more operational features. For example, among other features, the drive assembly 12 may include a motor (e.g., as discussed above and/or other suitable motor), rubber feet, control electronics, drive circuitry, etc.

The control unit 14, which may be separate from the drive assembly 12 (e.g., as shown in FIG. 1) or may be included in the drive assembly 12, may include several features. For example, as shown in FIG. 1, the control unit 14 may include a display 30 and a control knob 32 (e.g., a motor speed (e.g., RPM or other speed) adjustment knob or other control knob). Additionally or alternatively, the control unit 14 may include one or more other features for controlling the drive mechanism and/or other features of the drive assembly 12 (e.g., one or more drive mechanism states of the drive mechanism) including, but not limited to, a processor, memory, input/output devices, a speaker, volume control buttons, on/off power supply switch, motor activation switch, a timer, a clock, and/or one or more other features.

In some cases, the control unit 14 may include one or more drive mechanism load output control mechanisms for controlling an operation of the atherectomy system 10. In one example of a drive mechanism load output control mechanism that may be included in the control unit 14, the control unit 14 may include a mechanism configured to set and/or adjust an advancing load output (e.g., a rotational speed) and/or a retracting load output from the drive mechanism 34. Additionally or alternatively, the control unit 14 may include other control and/or safety mechanism for controlling the operation of the atherectomy system 10 and mitigating risks to patients.

Figure 2:
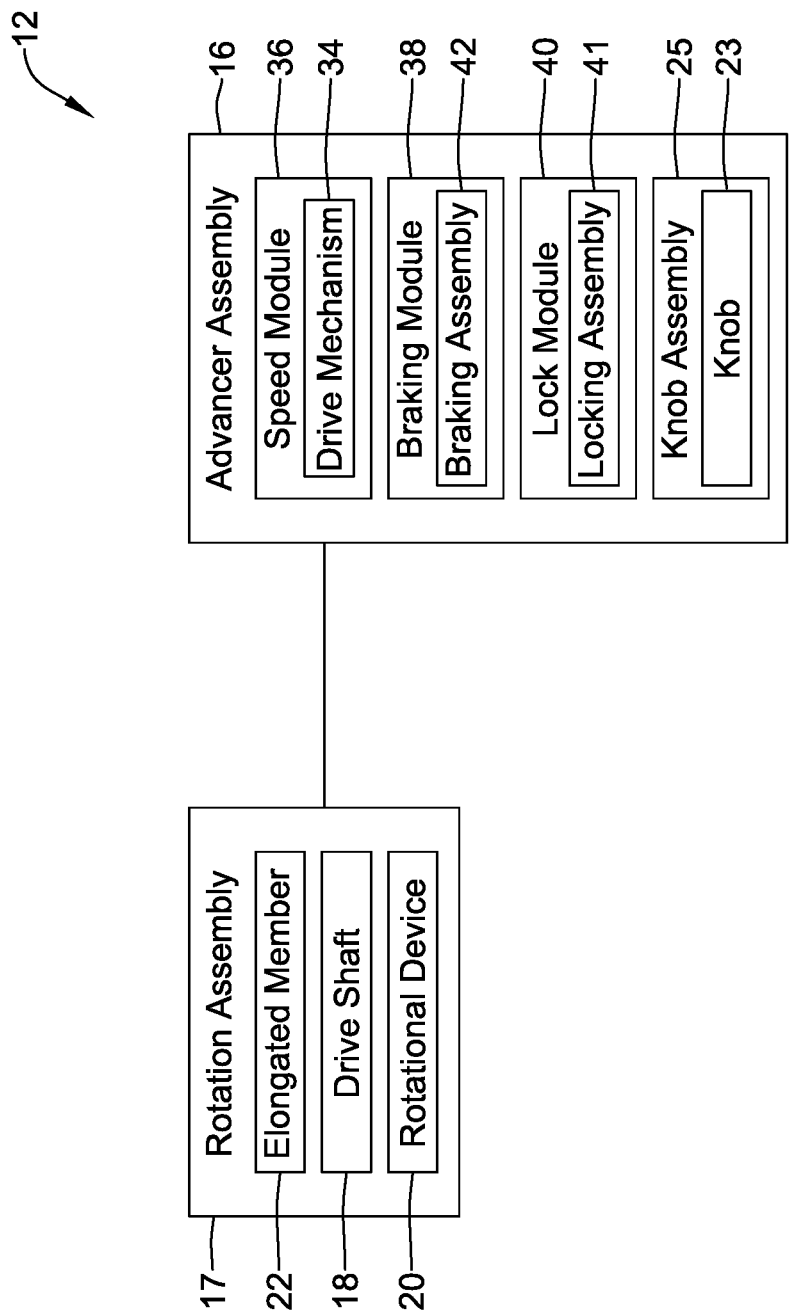
FIG. 2 is a schematic box diagram of an example drive assembly of an atherectomy system.

FIG. 2 depicts a box diagram of the drive assembly 12 including the rotation assembly 17 and the advancer assembly 16. As discussed above, the rotation assembly 17 may include, among other components, the drive shaft 18, the rotational device 20, and the elongate member 22. The advancer assembly 16 may include (e.g., at least partially within the housing 26 depicted in FIG. 1), among other components, a knob assembly 25, a speed module 36, a braking module 38, and a lock module 40.

The components of the advancer assembly 16 may be configured to communicate directly with one or more other components of the advancer assembly 16. Additionally or alternatively, the components of the advancer assembly 16 may communication with one or more other components of the advancer assembly 16 through electrical connections with a central controller having one or more processors, memory, and/or one or more other components of the advancer assembly 16.

The knob assembly 25 may be or may include the knob 23 (e.g., an actuator or actuation mechanism of the knob assembly 25) that may be at least partially accessible for adjustment and/or actuation from exterior of the housing 26 of the advancer assembly 16. Additionally or alternatively, the knob assembly 25 may include electrical connections, one or more processors, and/or memory to facilitate receiving input at the knob 23 and transferring signals to other components of the advancer assembly 16. The knob assembly 25 may be in direct or indirect (e.g., indirectly via the central controller and/or other components, if desired) communication with one or more of the speed module 36, the braking module 38, the lock module 40 and/or other components of drive assembly 12 through an electrical connection, a mechanical connection, and/or other suitable connections. In some cases, a single adjustment or actuation of the knob assembly 25 may be configured to change two or more settings of the modules of the advancer assembly 16

The knob 23 may be adjusted and/or actuated in one or more directions. For example, the knob 23 may be longitudinally adjustable to longitudinally adjust and/or position the knob assembly 25, the knob 23 may be configured to rotate in a clockwise direction and/or a counter-clockwise direction, the knob 23 may be configured to be actuated in an axial direction along an axis about which the knob 23 may rotate, and/or the knob 23 may be adjusted and/or actuated in one or more other suitable manners. In some cases, adjustment and/or actuation of the knob 23 may adjust one or more settings of one or more other components of the advancer assembly 16, as discussed in further detail below.

Although the FIGs. depict the knob 23 as being an actuator or actuation mechanism of the knob assembly 25, it is contemplated that the actuator or actuation mechanism of the knob assembly 25 may take on one or more other forms. For example, the knob assembly 25 may include an actuator or actuation mechanism being and/or having one or more of a physical button, a virtual button, a virtual knob, a physical knob, a touch sensitive surface, a shape other than what is depicted in the FIGs., one or more colors and/or color combinations, and/or other suitable feature configured for actuation or adjustment.

The speed module 36 may include or may be in communication with the drive mechanism 34 via an electrical connection, a mechanical connection, and/or other suitable connections, to adjust a desired speed setting of the drive mechanism 34. Additionally or alternatively, the knob assembly 25 may include electrical connections, one or more processors, and/or memory to facilitate receiving input signals initiated from the knob assembly 25 and using the received signals to directly or indirectly (e.g., indirectly via the central controller, if desired) control settings and/or operation of the drive mechanism 34.

In some cases, the speed module 36 may be configured to adjust a speed setting of the drive mechanism 34 between a zero (0) speed setting and one or more additional speed settings and/or actuate a mode of the drive mechanism 34 in response to input or communications received from the knob assembly 25 or the central controller. In one example, in response to a received input that is initiated by adjustment of the knob 23, the speed module 36 may be configured to adjust a speed setting between one of a zero (0) speed setting, a first speed setting (e.g., an advance speed setting), and a second speed setting (e.g., a withdraw or retract speed setting) and another one of the zero (0) speed setting, the first speed setting, and the second speed setting. In some cases, the first speed setting may be associated with a rotational speed for the rotational device 20 that facilitates advancement of the rotational device 20 through an obstruction or occlusion in a vessel of the patient and the second speed setting may be associated with a rotational speed for the rotational device 20 that facilitates withdrawal (e.g., retraction) of the rotational device 20 within the vessel while mitigating risks of injury to the patient. The second speed setting may be lower than the first speed setting in the above example, but this is not required. In another example, in response to a received input that is initiated by actuation or adjustment of the knob 23, the speed module 36 may actuate the drive mechanism 34 between an off mode and an on mode to initiate rotation of the drive mechanism 34 at a desired or set speed setting and accordingly rotate the rotational device 20.

The braking module 38 may include a braking assembly 42 configured to engage a guidewire extending through the advancer assembly 16 and prevent rotation of the guidewire when the drive shaft 18 and/or the rotational device 20 rotate. Additionally or alternatively, the braking module 38 may include electrical connections, a processor, and/or memory configured to directly or indirectly (e.g., indirectly via the central controller, if desired) receive communications and/or other suitable inputs initiated by adjustment of the knob assembly 25 and adjust a brake setting (e.g., between an activated setting and a deactivated setting and/or between other suitable settings) of the braking assembly 42 in response to the communications and/or other inputs received. In one example, when the braking module 38 has set the braking assembly 42 to a deactivated setting, adjustment of the knob assembly 25 may result in initiating a signal to the braking module 38 for the braking assembly 42 to enter an activated setting and engage a guidewire extending through the advancer assembly 16. Then, further adjustment of the knob assembly 25 may result in initiating a signal to the braking module 38 for the braking assembly 42 to enter a deactivated setting and disengage the guidewire to allow the rotation assembly 17 to be withdrawn over the guidewire.

The braking assembly 42 may engage the guidewire extending through the advancer assembly 16 via a friction fit, a pinch fit, a pressure fit, and/or one or more other suitable types of engagement when in an activated setting. In one example braking assembly 42 may be an electromechanical brake system configured to receive an electrical signal and in response to the electrical signal, either grasp the guidewire extending through the advancer assembly 16 or let go of the guidewire extending through the advancer assembly 16. Alternatively, the braking assembly 42 may be mechanical in nature and may be initiated through mechanical initiation. In an example of a mechanical braking assembly 42, the braking assembly 42 may adjust and grasp or otherwise engage the guidewire extending through the housing 26 of the advancer assembly 16 as the knob 23 rotates. Other mechanical and/or electromechanical braking configurations are contemplated.

The lock module 40 may include a locking assembly 41 to lock the knob assembly 25 at a longitudinal location along the housing 26 of the advancer assembly 16 in response to communications and/or other suitable inputs initiated by the knob assembly 25. Additionally or alternatively, the locking assembly 41 may include electrical connections, a processor, and/or memory configured to directly or indirectly (e.g., indirectly via the central controller or other suitable components, if desired) receive the communications and/or other suitable inputs initiated by adjustment of the knob assembly 25 and adjust a lock setting (e.g., between and activated setting and a deactivated setting and/or between other suitable settings) of the locking assembly 41 in response to the communications and/or other inputs received. In one example, when the lock module 40 has set the locking assembly 41 to a deactivated setting, adjustment of the knob assembly 25 may result in initiating a signal to the lock module 40 for the locking assembly 41 to enter an activated setting and prevent the knob assembly 25 from adjusting longitudinally with respect to the housing 26 of the advancer assembly 16. Then, further adjustment of the knob assembly 25 may result in initiating a signal to the lock module 40 for the locking assembly 41 to enter a deactivated setting and allow the knob assembly 25 to adjust longitudinally with respect to the housing 26 of the advancer assembly 16.

The locking assembly 41 may be configured to lock the knob assembly 25 at a longitudinal location along the housing 26 of the advancer assembly 16 in one or more suitable manners. In one example, the locking assembly 41 may be configured to engage the housing 26 or a feature extending from the housing 26 via a friction fit, a pinch fit, a pressure fit, and/or one or more other suitable types of engagement when in an activated setting. In one example, the locking assembly may be an electromechanical lock system configured to receive an electrical signal and in response to receiving the electrical signal, either engage the housing 26 and/or other component of the advancer assembly 16 or disengage the housing 26 and/or other component of the advancer assembly 16. Alternatively, the locking assembly 41 may be mechanical in nature and may be initiated through mechanical initiation. In an example of a mechanical locking assembly 41, the locking assembly 41 may rotate and engage the housing 26 of the advancer assembly 16 as the knob 23 is rotating. In another example, the locking assembly 41 may be biased in a lock position and move to an unlocked position in response to actuation. Other mechanical and/or electromechanical locking configurations are contemplated.

FIGS. 3A-3D depict the example advancer assembly 16 showing the knob assembly 25 in various modes based on position configurations of the knob 23, where each mode of the knob assembly 25 is configured to set settings of various modules to predetermined settings. The described modes of the knob assembly 25 and associated settings for modules of the advancer assembly 16 are illustrative and it is contemplated other modes of the knob assembly 25 and/or settings of the modules may be utilized, as desired. Although the knob 23 is depicted and described as being associated with modes of the knob assembly 25 at quarter (¼) turn positions in FIGS. 3A-3D (e.g., where a full turn is 360 degrees), it is contemplated that the knob 23 may be positioned and/or associated with one or modes of the knob assembly 25 at any suitable rotatable position relative to a full turn of the knob 23 (e.g., half (½) turns, eighth (⅛) turns, three quarter (¾) turns, other suitable partial or full turns, and the like).

Figure 3A:
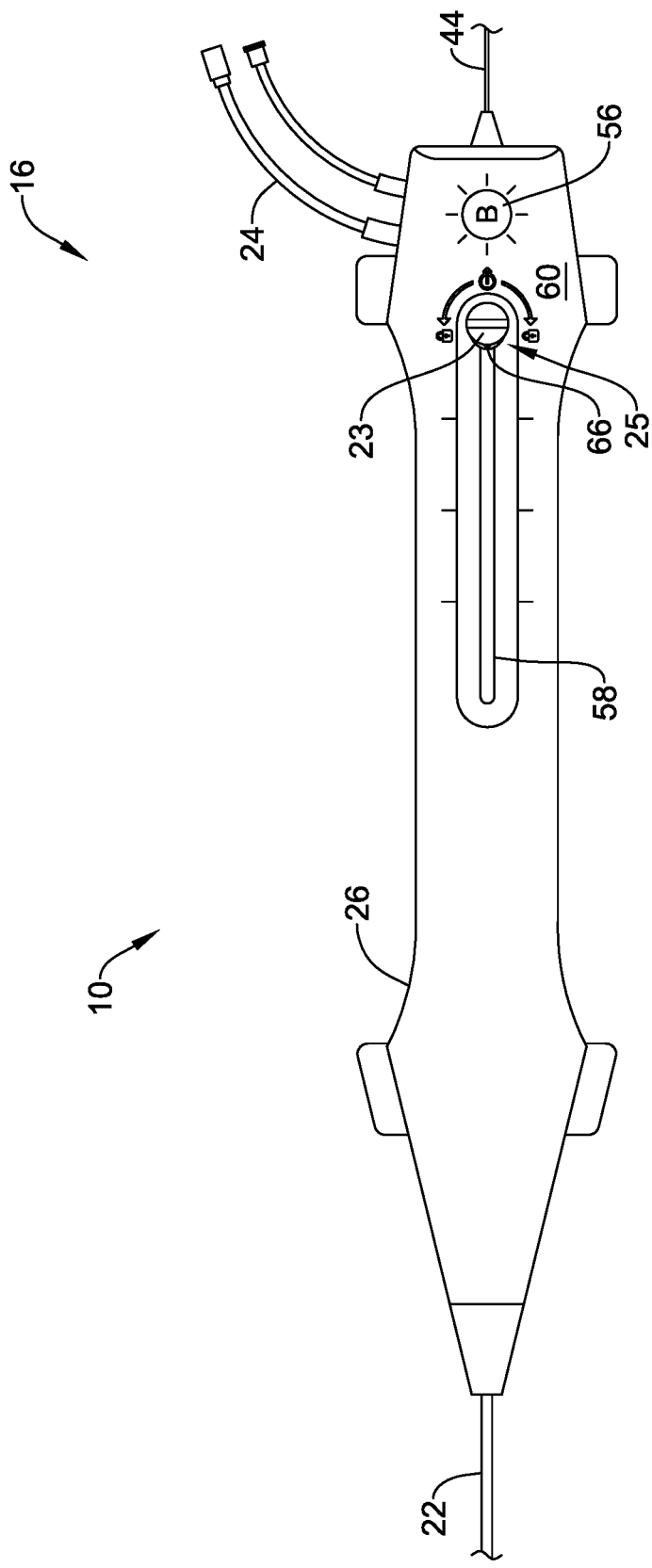
FIG. 3A is a schematic top view of a portion of an example atherectomy system in an advance configuration.
Figure 3B:
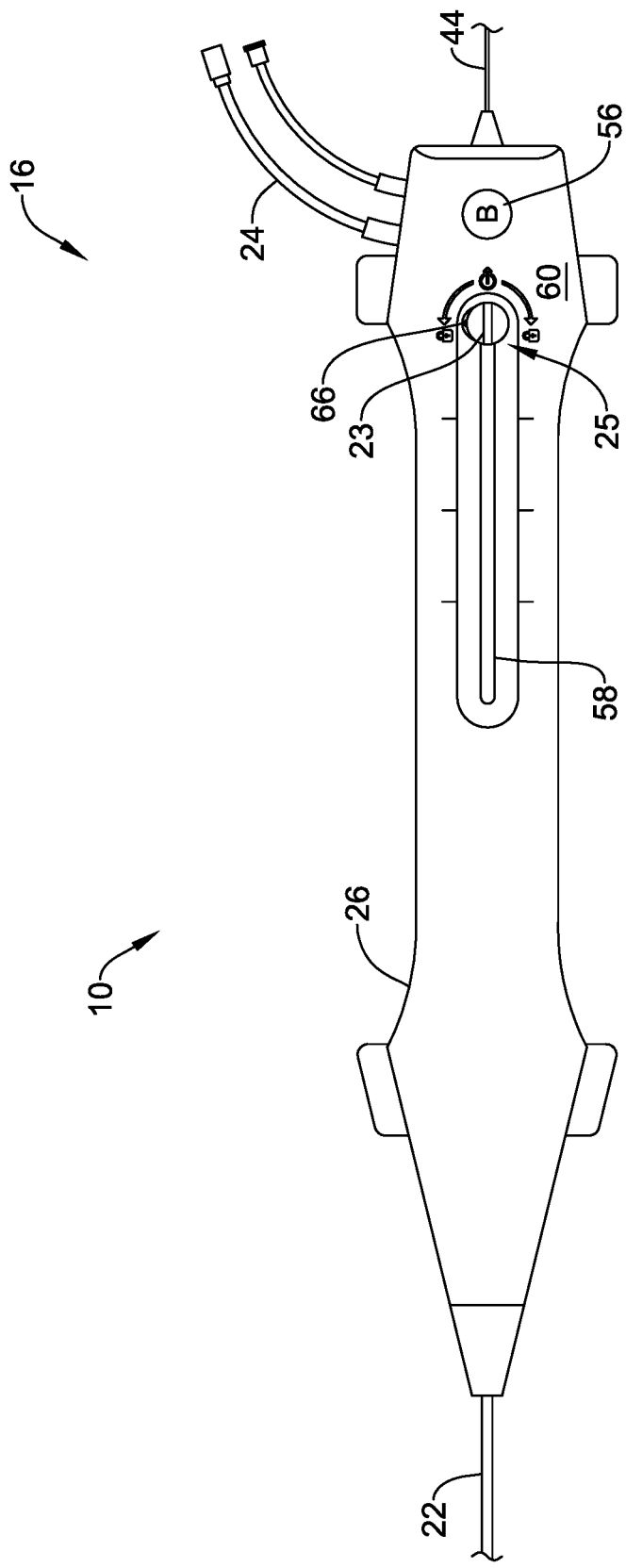
FIG. 3B is a schematic top view of the portion of the example atherectomy system depicted in FIG. 3A in a locked configuration.
Figure 3C:
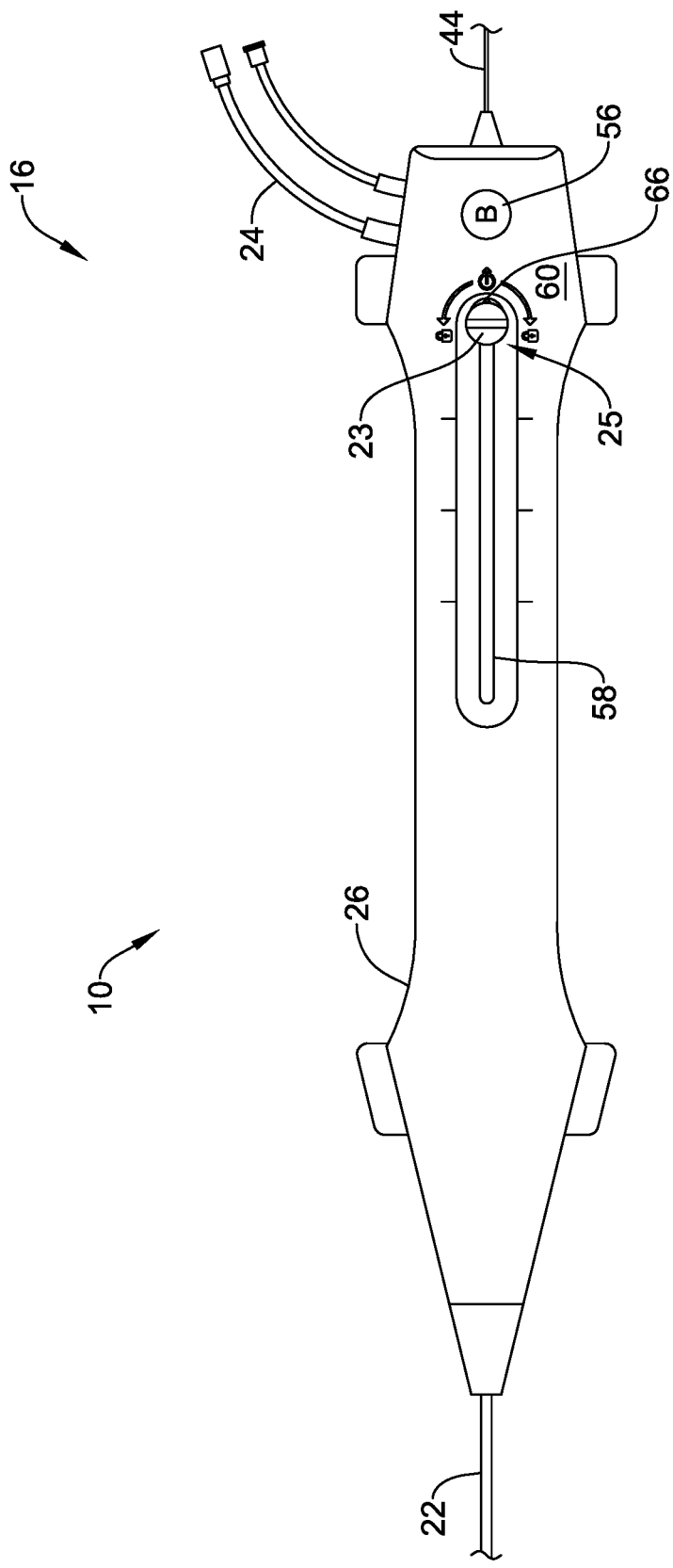
FIG. 3C is a schematic top view of the portion of the example atherectomy system depicted in FIG. 3A in a withdraw configuration.
Figure 3D:
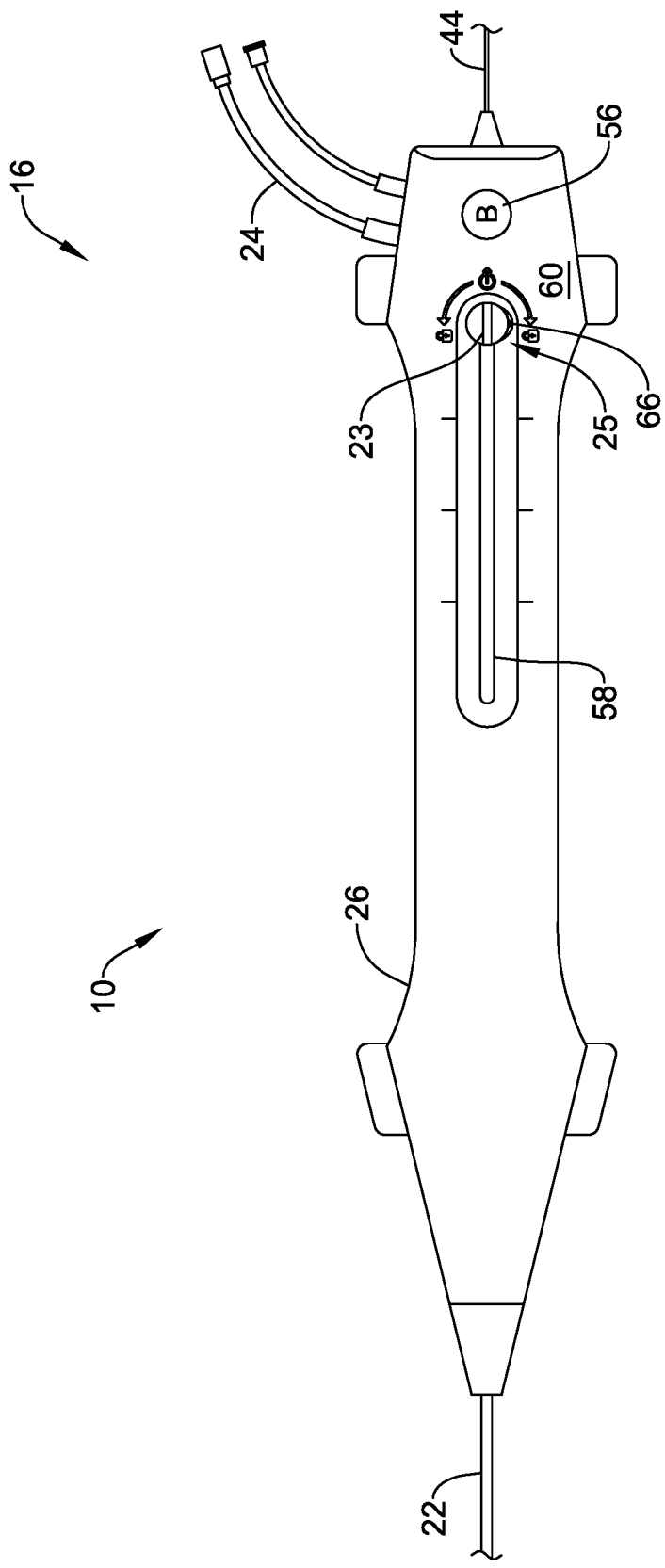
FIG. 3D is a schematic top view of the portion of the example atherectomy system depicted in FIG. 3A in a locked configuration.

FIG. 3A depicts the advancer assembly 16 with the knob 23 in a distal or forward configuration and setting the knob assembly 25 to an advance mode. FIG. 3B depicts the advancer assembly 16 with the knob 23 in an upward configuration and setting the knob assembly 25 to a lock mode. FIG. 3C depicts the advancer assembly 16 with the knob 23 in a proximal or backward configuration and setting the knob assembly 25 to a withdraw mode. FIG. 3D depicts the advancer assembly 16 with the knob 23 in a downward configuration and setting the knob assembly 25 to the lock mode. Although FIGS. 3A-3D depict the knob 23 sequentially adjusted in a clockwise direction, it is contemplated that the knob 23 may be rotated in a counter-clockwise direction.

In some cases, the knob 23 or the knob assembly 25 may include a knob indicator that indicates or points to a configuration of the knob 23 and a mode of the knob assembly 25. In the example of FIGS. 3A-3D, the knob 23 may include a knob indicator 66. The knob indicator 66 may be a dot on, an arrow-shaped portion of, the inherent shape of the knob 23, color of the knob 23, or other suitable configuration on or of the knob 23, as desired.

The advancer assembly 16 may include, as discussed above, the knob assembly 25, the speed module 36, the braking module 38, and the lock module 40, and one or more settings of the speed module 36, the braking module 38, and/or the lock module 40 may be adjusted in response to adjustment and/or actuation of the of the knob 23 between the example configurations depicted in FIGS. 3A-3D and/or other suitable configurations. Such a configured advancer assembly 16 of an atherectomy system 10 may facilitate limiting a number of steps required to prepare settings for different modules or components of the atherectomy system 10 prior to and/or during use of the atherectomy system 10 in a procedure. For example, adjusting the knob 23 to point distally or forward, as depicted in FIG. 3A and discussed in greater detail below, or other single adjustment of an actuator or actuation mechanism may adjust settings of the speed module 36, the braking module 38, and/or the lock module 40 for advancement of a rotational device (e.g., the rotational device 20 or other suitable rotational device) within a vessel of a patient, whereas in previous atherectomy systems it was necessary to separately adjust a speed setting (e.g., with a foot pedal), adjust a brake setting (e.g., on an advancer assembly), and adjust a lock mechanism (e.g., at a knob) to prepare the atherectomy system for advancement of the rotational device within a vessel of a patient. The single adjustment of an actuator or actuator mechanism to adjust settings of multiple components of the atherectomy system 10 mitigates human error by requiring fewer steps when changing how the atherectomy system is being used (e.g., between advancement and retraction, etc.).

To further facilitate ease of use of the atherectomy system 10 and as depicted in FIGS. 3A-3D, the housing 26 of the advancer assembly 16 may include indicia on an outer surface 60. When included, the indicia on the housing 26 may include, but is not limited to, descriptive indicia indicating a mode in which the knob assembly 25 is positioned. This indicia may be graphical representations of the modes in which the knob assembly 25 is positioned (e.g., a lock icon representing a lock mode, a retract icon representing a retract mode, etc.). Additionally or alternatively, indicia may be provided at predetermined and/or consistent locations along an opening 58 to provide a user (e.g., a physician or other user) with a measurement or other indication of an axial position of the drive mechanism 34, the drive shaft 18, and/or the rotational device 20. Such indicia may be tick marks, measurements (e.g., millimeters, centimeters, inches, etc.), and/or other suitable indicia that facilitate providing an understanding of a relative position of the knob assembly 25 and/or the drive mechanism 34 along the opening 58. Additionally or alternatively, the shape and/or color of the knob 23 may indicate a mode in which the knob assembly 25 is positioned (e.g., the knob 23 may include one or more colors, where the color of the knob 23 at a predetermined position (e.g., a forward position, a backward position, a side position, a position aligned with indicia on the housing 26, and/or other suitable predetermined position) indicates a current mode of the knob assembly 25). Further, in some cases, a brake indicator 56 may be included on and/or adjacent the outer surface 60 of the housing 26 to indicate (e.g., by luminescence, LED, digital display, and/or other suitable types of indicia) to a user that the braking assembly 42 is in one of an activated mode and a deactivated mode.

FIG. 3A depicts an example of the advancer assembly 16 showing the knob assembly 25 in the advance mode. When the knob assembly 25 is set to the advance mode, the knob indicator 66 of or in communication with the knob 23 may be directed toward a distal end of the advancer assembly 16. Although various modes of the knob assembly 25 and/or setting of modules of the advancer assembly 16 may be described as being associated with a position of the knob 23 or direction of the knob indicator 66, the modes and/or settings of modules may be associated with any suitable position of the knob 23 or direction of the knob indicator 66.

When the knob assembly 25 is set to the advance mode, a signal may be initiated such that the braking module 38 may receive a signal to adjust a brake setting to an activated setting. When the braking module 38 is in the activated brake setting, the braking assembly 42 may engage a guidewire 44, as discussed above with respect to FIG. 2, and may restrict movement (e.g., rotational and/or longitudinal movement) of the guidewire 44 relative to the rotation assembly 17 and/or the advancer assembly 16. Further, when the braking module 38 is in the activated setting, the brake indicator 56 may be illuminated, as shown for example in FIG. 3A, or turned off to indicate the braking module 38 is in the activated setting.

Further, the signal initiated when the knob assembly 25 is set to the advance mode may result in the lock module 40 receiving a signal to adjust a lock setting to a deactivated setting. When the lock module 40 is in the deactivated lock setting, the locking assembly 41 may unlock the knob assembly 25 relative to the housing 26 of the advancer assembly 16. Unlocking the knob assembly 25 relative to the housing 26 may allow for movement of the knob 23 along the longitudinal slot or opening 58 to advance and/or withdraw the rotational device 20 (not shown in FIGS. 3A-3D) in communication with knob assembly 25 with respect to the advancer assembly 16. In some cases, tick marks or other indicia along the longitudinal slot or opening 58 may indicate to a user how far the rotational device has been advanced as the knob 23 adjusts longitudinally.

Further, the signal initiated when the knob assembly 25 is set to the advance mode may result in the speed module 36 receiving a signal to adjust a speed setting to a first speed setting (e.g., an advance speed setting). When the speed module 36 is in the first speed setting, the drive mechanism 34 may be set to operate at an advance speed. The advance speed may be a predetermined speed and/or adjustable speed at which the drive mechanism is to operate to rotate the rotational device 20 to facilitate passing an obstruction in a patient's vessel.

In some cases, when the speed module 36 adjusts the speed setting to a first speed setting, the speed module may automatically initiate movement of the drive mechanism 34 at the advance speed to rotate the rotational device 20. Alternatively, an actuation of the knob 23 or other actuator in addition to adjustment of the knob 23 to a distal or forward configuration may be required to initiate movement of the drive mechanism 34, as discussed for example with respect to FIGS. 4A-4E. Requiring such actuation of the knob 23 or other actuator in addition to adjustment of the knob 23 to a distal or forward configuration to initiate movement of the drive mechanism 34 may allow for a user of the atherectomy system 10 to have the knob assembly 25 in the advance mode without rotation of the rotational device 20.

FIG. 3B depicts an example of the advancer assembly 16 showing the knob assembly 25 in the lock mode. When the knob assembly 25 is set to the lock mode from the advance mode, the knob indicator 66 of or in communication with the knob 23 may have been adjusted in a clockwise direction such that the knob indicator 66 is directed upward and/or substantially perpendicular to a longitudinal axis of the advancer assembly 16.

When the knob assembly 25 is set to the lock mode, a signal may be initiated such that the braking module 38 may receive a signal to adjust a brake setting to a deactivated setting. When the braking module 38 is in the deactivated brake setting, the braking assembly 42 may disengage the guidewire 44 to allow and/or facilitate movement (e.g., rotational and/or longitudinal movement) of the guidewire 44 relative to the rotation assembly 17 and/or the advancer assembly 16. Further, when the braking module 38 is in the deactivated setting, the brake indicator 56 may be turned off or otherwise not illuminated, as shown for example in FIG. 3B, or turned on to indicate the braking module 38 is in the deactivated setting.

Further, the signal initiated when the knob assembly 25 is set to the lock mode may result in the lock module 40 receiving a signal to adjust a lock setting to an activated setting. When the lock module 40 is in the activated lock setting, the locking assembly 41 may lock the knob assembly 25 relative to the housing 26 of the advancer assembly 16. Locking the knob assembly 25 relative to the housing 26 may restrict or prevent movement of the knob 23 along the longitudinal slot or opening 58 to restrict or prevent longitudinal movement (e.g., advancing or withdrawing) of a rotational device in communication with knob assembly 25 with respect to the advancer assembly 16.

Further, the signal initiated when the knob assembly 25 is set to the lock mode may result in the speed module 36 receiving a signal to adjust a speed setting to a zero (0) speed setting (e.g., a stop speed setting). When the speed module 36 is in the zero (0) speed setting, the drive mechanism 34 may be set to prevent operation of the drive mechanism 34 and thus, rotation of the rotational device 20. Accordingly, when the speed module is in the zero (0) speed setting, the drive mechanism 34 may not operate or cause rotation of the rotational device 20 even in response to the knob 23 or other actuator being actuated to initiate operation of the drive mechanism 34 because the drive mechanism 34 is set to operate at a zero (o) speed.

FIG. 3C depicts an example of the advancer assembly 16 showing the knob assembly 25 in the withdraw mode. When the knob assembly 25 is set to the withdraw mode, the knob indicator 66 of or in communication with the knob 23 may be adjusted in a clockwise direction such that the knob indicator 66 is directed toward a proximal end of the advancer assembly 16.

When the knob assembly 25 is set to the withdraw mode, a signal may be initiated such that the braking module 38 may receive a signal to adjust or maintain a brake setting to or in a deactivated setting. When the braking module 38 is in the deactivated brake setting, the braking assembly 42 may disengage or be disengaged from the guidewire 44 to allow or facilitate movement (e.g., rotational and/or longitudinal movement) of the guidewire 44 relative to the rotation assembly 17 and/or the advancer assembly 16. Further, when the braking module 38 is in the deactivated setting, the brake indicator 56 may be turned off or otherwise not illuminated, as shown for example in FIG. 3C, or turned on to indicate the braking module 38 is in the deactivated setting.

Further, the signal initiated when the knob assembly 25 is set to the withdraw mode may result in the lock module 40 receiving a signal to adjust a lock setting to a deactivated setting. When the lock module 40 is in the deactivated lock setting, the locking assembly 41 may unlock the knob assembly 25 relative to the housing 26 of the advancer assembly 16. Unlocking the knob assembly 25 relative to the housing 26 may allow for movement of the knob 23 along the longitudinal slot or opening 58 to advance and/or withdraw the rotational device 20 in communication with knob assembly 25 with respect to the advancer assembly 16. In some cases, tick marks or other indicia along the longitudinal slot or opening 58 may indicate to a user how far the rotational device has traveled as the knob 23 adjusts longitudinally.

Further, the signal initiated when the knob assembly 25 is set to the withdraw mode may result in the speed module 36 receiving a signal to adjust a speed setting to a second speed setting (e.g., a withdraw speed setting). When the speed module 36 is in the second speed setting, the drive mechanism 34 may be set to operate at a withdraw speed. The withdraw speed may be a predetermined speed and/or adjustable speed at which the drive mechanism is to operate to rotate the rotational device 20 to withdraw the rotational device 20 within the vessel of the patient. In some cases, the second speed setting or withdraw speed setting may be a lower speed than the first speed setting or advance speed setting. The withdraw speed setting may be configured to facilitate removal of the rotational device 20 from the patient's vessel and can be lower than the advance speed setting, as the rotational device 20 is not typically trying to burr through an obstruction in the patient's vessel when the knob assembly 25 is in the withdraw mode. In some cases, the withdraw speed setting may be configured to break up friction of the rotation assembly 17 with the guidewire 44 and/or other friction inhibiting withdrawal of the rotation assembly 17.

Similar to as discussed above with respect to FIG. 3A, when the speed module 36 adjusts the speed setting to a second speed setting, the speed module may automatically initiate movement of the drive mechanism 34 at the withdraw speed to rotate the rotational device 20. Alternatively, an actuation of the knob 23 or other actuator in addition to adjustment of the knob 23 to a proximal or backward configuration may be required to initiate movement of the drive mechanism 34, as discussed for example with respect to FIGS. 4A-4E. Requiring such actuation of the knob 23 or other actuator in addition to adjustment of the knob 23 to a proximal or backward configuration to initiate movement of the drive mechanism 34 may allow for a user of the atherectomy system 10 to have the knob assembly 25 in the withdraw mode without rotation of the rotational device 20.

FIG. 3D depicts an example of the advancer assembly 16 showing the knob assembly 25 in the lock mode. When the knob assembly 25 is set to the lock mode from the withdraw mode, the knob indicator 66 of or in communication with the knob 23 may have been adjusted in a clockwise direction such that the knob indicator 66 is directed downward or substantially perpendicular to a longitudinal axis of the advancer assembly 16. Such adjustment of the knob 23 to place the knob assembly 25 in the lock mode may result in initiating a signal such that the braking module 38, the lock module 40, and/or the speed module 36 receive signals to set settings similar to as discussed above with respect to FIG. 3B. Alternatively or in addition, one or more of the braking module 38, the lock module 40, and/or the speed module 36 may receive signals to adjust one or more setting in a manner different than discussed above with respect to FIG. 3B.

Figure 4A:
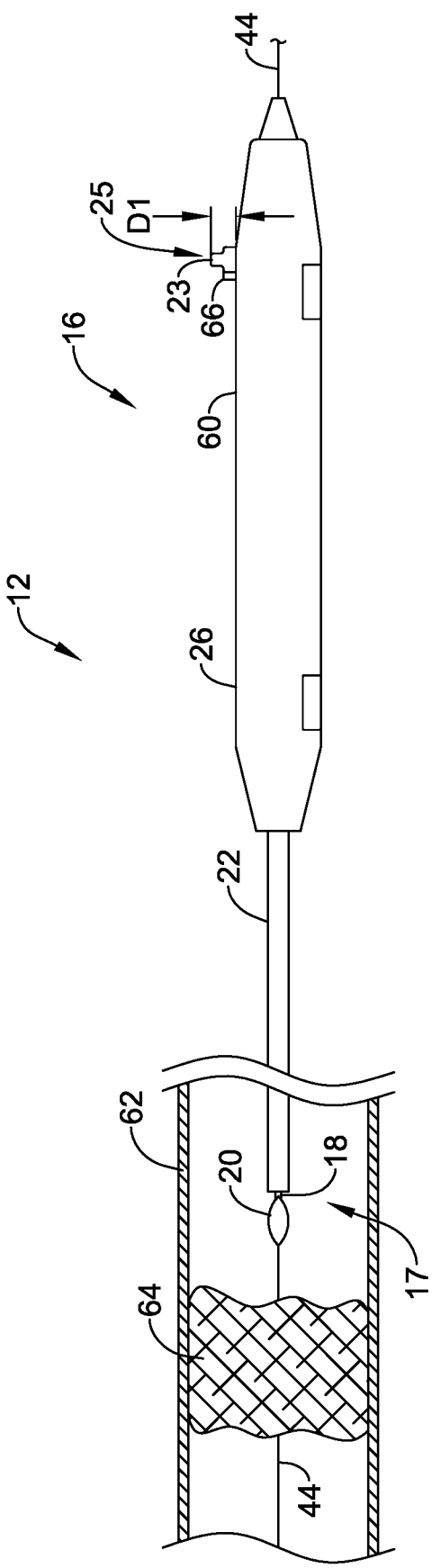
FIG. 4A is a schematic side view of a portion of an example atherectomy system inserted in a vessel with the vessel shown in cross-section and the example atherectomy system in an advance configuration.
Figure 4B:
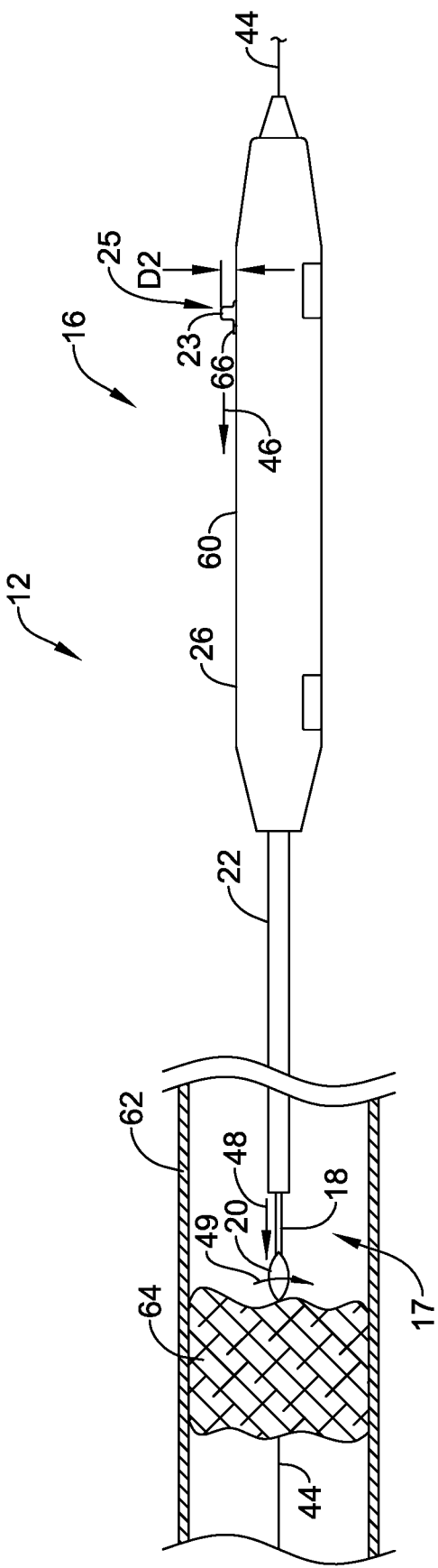
FIG. 4B is a schematic side view of the portion of the example atherectomy system depicted in FIG. 4A in the advance configuration with a rotational device rotating and advancing within the vessel.
Figure 4C:
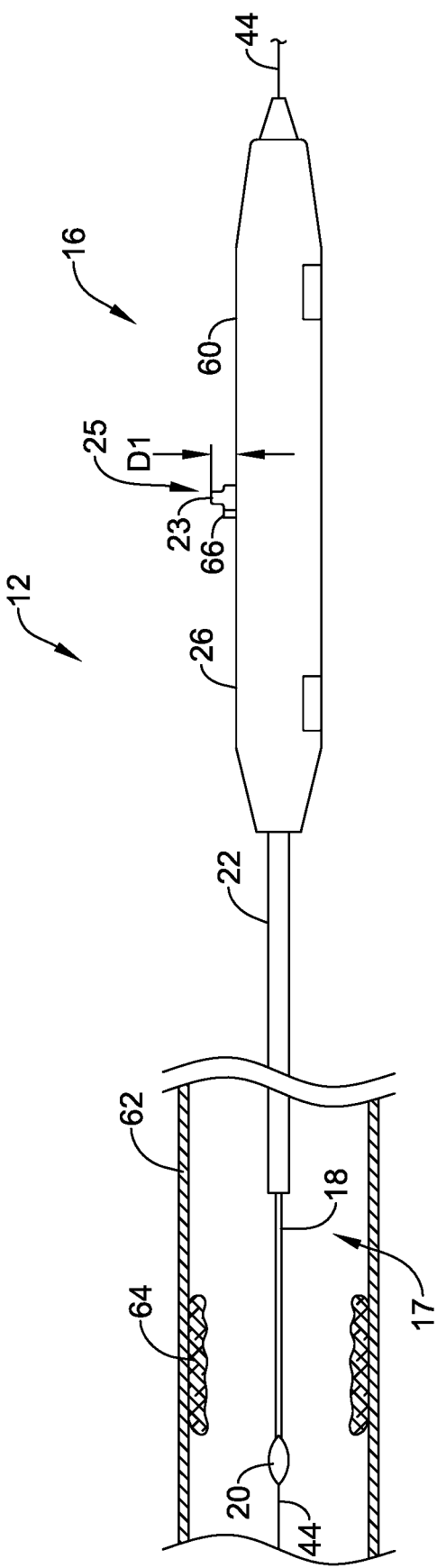
FIG. 4C is a schematic side view of the portion of the example atherectomy system depicted in FIG. 4A in an off configuration while fully advanced.
Figure 4D:
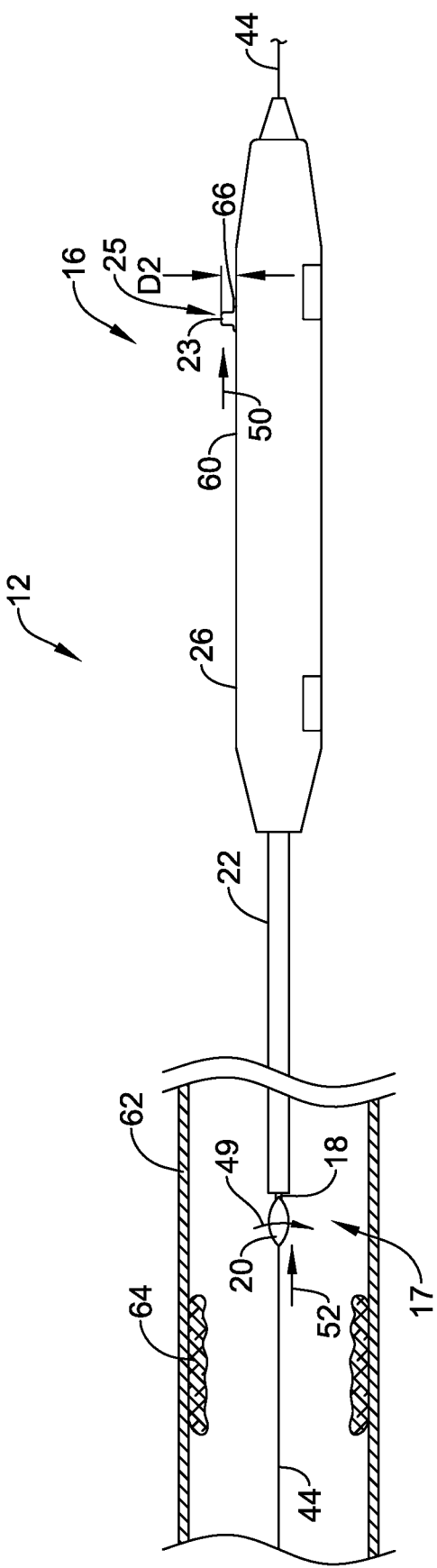
FIG. 4D is a schematic side view of the portion of the example atherectomy system depicted in FIG. 4A in a withdrawal configuration with the rotational device rotating and withdrawing within the vessel.
Figure 4E:
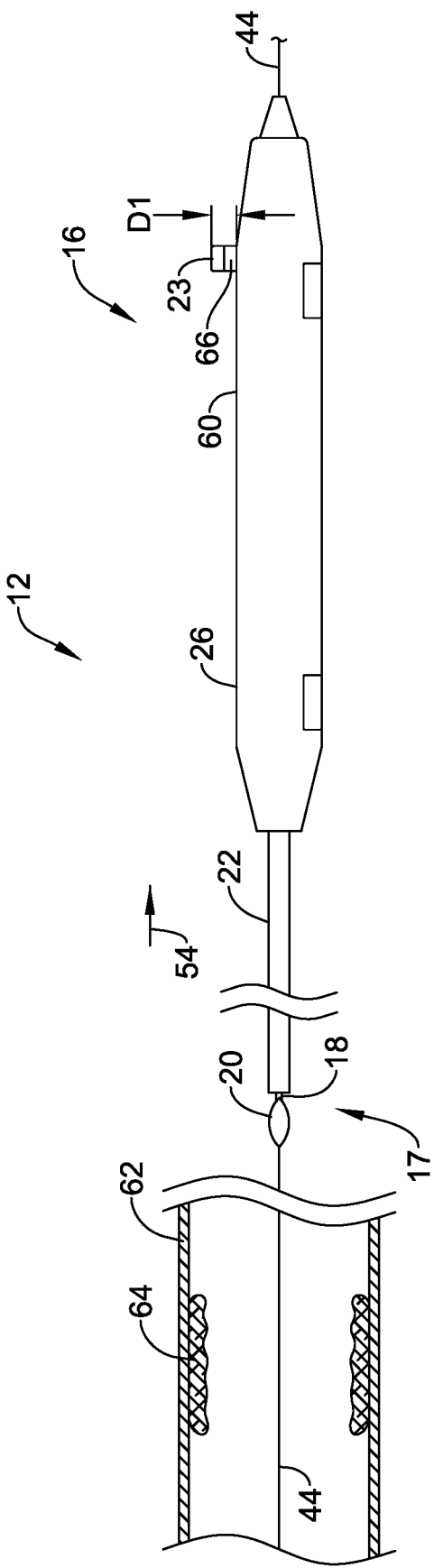
FIG. 4E is a schematic side view of the portion of the example atherectomy system depicted in FIG. 4A in a locked configuration with the rotational device fully withdrawn from the vessel.

FIGS. 4A-4E depict side views of the drive assembly 12 of the atherectomy system 10 showing schematic views of an example method of using the atherectomy system 10 to advance through a vessel 62 of a patient and pass an occlusion 64 within the vessel 62, where the vessel 62 and the occlusion 64 are depicted in cross-section. FIG. 4A depicts the atherectomy system 10 inserted into a patient's vessel 62 over the guidewire 44, with the rotational device 20 not rotating and proximal of the occlusion 64. FIG. 4B depicts the atherectomy system 10 inserted into the patient's vessel 62 over the guidewire 44, with the rotational device 20 rotating and being advanced toward the occlusion 64. FIG. 4C depicts the atherectomy system 10 inserted into the patient's vessel 62 over the guidewire 44, with the rotational device 20 not rotating and advanced through the occlusion 64. FIG. 4D depicts the atherectomy system 10 inserted into the patient's vessel 62 over the guidewire 44, with the rotational device 20 rotating and being withdrawn from the occlusion 64. FIG. 4E depicts the atherectomy system 10 withdrawn from the patient's vessel 62 over the guidewire 44, with the rotational device 20 not rotating.

As shown in FIG. 4A, the drive shaft 18, the rotational device 20, and the elongate member 22 of the drive assembly 12 have been inserted over the guidewire 44 into a vessel 62 of a patient to a location proximal of the occlusion 64. Typically, the drive assembly 12 may be inserted into the vessel 62 while the knob assembly 25 is in the lock mode, and when the rotational device 20 is located at a target location proximal of the occlusion 64, the knob 23 may be rotated such that the knob assembly 25 is in an advance mode, as shown in FIG. 4A. As the knob assembly 25 is in the advance mode, the braking module 38 may be set to an activated setting, the lock module 40 may be set to a deactivated setting, and the speed module 36 may be set to an advance speed setting.

As can be seen in FIG. 4A, the rotational device 20 is not rotating even though the knob assembly 25 is in the advance mode. As such, actuation of the knob 23 may be required to initiate rotation of the rotational device 20 based on the advance setting for the drive mechanism 34 (not shown in FIG. 4A) within the housing 26 of the advancer assembly 16

As depicted in FIGS. 4A-4E, the knob 23 may be actuated by pressing on or applying a force to a top of the knob 23. Thus, when the knob 23 has not been actuated, there may be a distance D1 between an outer surface 60 of the housing 26 and the top of the knob 23. The knob 23 may be biased (e.g., via a spring or other suitable biasing mechanism) to the unactuated state, but this is not required. Although the FIGS. 4A-4E depict actuating the knob 23 by applying a force to a top of the knob 23, the knob 23 and/or other suitable actuator may be actuated in one or more different suitable manners (e.g., an actuator located elsewhere on the advancer assembly 16) to initiate movement of the drive mechanism 34.

FIG. 4B depicts the knob assembly 25 in the advance mode and the knob 23 in an actuated state, with a force (not shown) pressed on or otherwise applied to the top of the knob 23 to cause movement of the drive mechanism 34 and rotation of the rotational device 20 in the direction of rotational arrow 49. When the knob 23 is actuated, there may be a distance D2 between the outer surface 60 of the housing 26 and the top of the knob 23. This distance D2 may be less than the distance D1, but this is not required in all instances.

While the knob 23 is actuated and the rotational device 20 is rotating based on the advance mode of the drive mechanism 34, the knob 23 may be longitudinally advanced along the housing 26 in the direction of arrow 46. Advancing the knob 23 in the direction of the arrow 46 may cause the drive shaft 18 and the rotational device 20 to advance toward and/or into the occlusion 64 in the direction of arrow 48 while the rotational device 20 is rotating to burr through the occlusion 64.

Once the rotational device 20 has crossed the occlusion 64, as depicted in FIG. 4C, the force pressed on or otherwise applied to the top of the knob 23 may be removed and the knob 23 may return to unactuated state, where a distance between the outer surface 60 of the housing 26 and the top of the knob 23 is the distance D1.

After crossing the occlusion or at one or more other times, the knob 23 may be adjusted such that the knob assembly 25 is in the withdraw mode, as depicted in FIG. 4D. As the knob assembly 25 is in the withdraw mode, the braking module 38 may be set to the deactivated setting, the lock module 40 may be set to the deactivated setting, and the speed module 36 may be set to a withdraw speed setting. Further, the knob 23 in FIG. 4D is in an actuated state, with a force pressed on or otherwise applied to the top of the knob 23 to cause movement of the drive mechanism 34 and rotation of the rotational device 20 in the direction of the rotational arrow 49 and at a speed associated with the withdraw speed setting of the drive mechanism 34. Alternatively, actuation of the knob 23 while the knob assembly 25 is in the withdraw mode may cause rotation of the rotational device 20 in a direction opposite of the direction of the rotational arrow 49. When the knob 23 has been actuated and the rotational device 20 is rotating on the withdraw setting of the drive mechanism 34, the knob 23 may be longitudinally withdrawn along the housing in the direction of arrow 50. Axially translating the knob 23 in the direction of the arrow 50 may cause the drive shaft 18 and the rotational device 20 to withdraw within the vessel 62 in the direction of arrow 52 while the rotational device 20 is rotating.

The steps of advancing the rotational device 20 across the occlusion 64 and withdrawing the rotational device 20 may be repeated until the occlusion 64 has been sufficiently addressed (e.g., partially or fully removed or broken apart). Once, the occlusion 64 has been sufficiently addressed, the knob 23 may be fully withdrawn along the housing 26 and adjusted such that the knob assembly 25 is in the lock mode, as depicted in FIG. 4E. As the knob assembly 25 is in the lock mode, the braking module 38 may be set to the deactivated setting, the lock module 40 may be set to the activated setting, and the speed module 36 may be set to a zero (0) speed setting. Once the knob assembly 25 is in the lock mode, the advancer assembly 16 may be moved in the direction of arrow 54 relative to the vessel 62 to withdraw the drive shaft 18, the rotational device 20, and/or the elongate member 22 from the vessel 62.

Although not necessarily depicted in the FIGs., the methods and system described herein may include one or more steps other than those steps described herein and/or the described steps may be performed in one or more other orders, as desired unless expressly indicated otherwise. Moreover, the methods described herein may be repeated during operation of the atherectomy system 10 upon request or initiation, continuously, continuously at predetermined intervals, and/or at other times. Additionally, one or more additional medical devices including, but not limited to, a guide catheter, sheath, introducer, a filter, and/or other suitable medical devices not necessarily described or discussed herein may be utilized with the atherectomy system 10 to facilitate use of the atherectomy system 10 in vasculature of a patient.

Those skilled in the art will recognize that the present disclosure may be manifested in a variety of forms other than the specific embodiments described and contemplated herein. For instance, as described herein, various embodiments include one or more modules described as performing various functions. However, other embodiments may include additional modules that split the described functions up over more modules than that described herein. Additionally, other embodiments may consolidate the described functions into fewer modules.

Although various features may have been described with respect to less than all embodiments, this disclosure contemplated that all those features may be included on any embodiment. Further, although the embodiments described herein may have omitted some combinations of the various described features, this disclosure contemplates embodiments that include any combination of each described feature. Accordingly, departure in form and detail may be made without departing from the scope and spirit of the present disclosure as described in the appended claims.

What is claimed is:

1. An advancer assembly for an atherectomy device, comprising:
   a housing;
   a motor positioned within the housing;
   a knob assembly comprising a knob slidable along the housing; and
   wherein a first rotation of the knob causes the knob assembly to output a signal configured to cause a speed module to adjust a speed setting of the motor from a first speed setting to a second speed setting, wherein a second rotation of the knob further adjusts the speed setting of the motor from the second speed setting to a third speed setting, and wherein the first speed setting, the second speed setting, and the third speed setting are different.

2. The advancer assembly of claim 1, wherein the knob assembly further comprises:

memory; and a processor; and wherein the memory and processor are configured to facilitate transferring the signal to the speed module.

3. The advancer assembly of claim 1, wherein the signal is configured to initiate actuation of the motor according to the second speed setting.

4. The advancer assembly of claim 1, wherein the first rotation of the knob causes the knob assembly to output a signal configured to cause one or both of a braking module and a lock module to adjust a setting.

5. The advancer assembly of claim 1, wherein the first rotation of the knob includes a rotation of the knob from a first position associated with a first mode of the knob assembly to a second position associated with a second mode of the knob assembly.

6. The advancer assembly of claim 5, wherein the second mode of the knob assembly is associated with the second speed setting and a setting of one or more both of a braking module and a lock module.

7. The advancer assembly of claim 1, wherein the first rotation of the knob adjusts the knob assembly from a first mode of operation to a second mode of operation and the second rotation of the knob adjusts the knob assembly from the second mode of operation to a third mode of operation.

8. An atherectomy device, comprising:

a knob assembly including a knob, wherein the knob is longitudinally adjustable and rotationally adjustable; and wherein in response to rotation of the knob, the knob assembly is configured to:

adjust from a first mode to a second mode, wherein the first mode and the second mode each control operation of two or more operation modules in communication with the knob assembly, and output signals associated with a change from the first mode to the second mode, and wherein the two or more operation modules include a speed module configured to adjust a speed setting of a motor and one or both of a locking module configured to lock or unlock the knob at a longitudinal location and a braking module configured to engage a guidewire.

9. The atherectomy device of claim 8, further comprising:

a housing and the motor positioned within the housing.

10. The atherectomy device of claim 9, wherein the knob is configured to adjust longitudinally along an exterior of the housing.

11. The atherectomy device of claim 9, further comprising:

a rotation assembly including an elongate member coupled to a rotational device at a distal end of the elongate member; and wherein a proximal end of the elongate member is in communication with the motor and actuation of the motor causes the rotational device to rotate.

12. The atherectomy device of claim 9, wherein the knob assembly is in electrical communication with the motor.

13. The atherectomy device of claim 8, wherein each of the first mode and the second mode are associated with predefined settings for each of the two or more operation modules.

* * * * *